United States Patent [19]  
Kuzmina et al.

[11] 4,000,422  
[45] Dec. 28, 1976

[54] METHOD OF LUMINESCENCE DETECTION OF SURFACE DISCONTINUITIES

[76] Inventors: Nadezhda Vasilievna Kuzmina, ulitsa Pushkina, 2/23, Moskovskaya oblast, Yaroslavskaya zheleznaya doroga, stantsiya Bolshevo; Ljudmila Ivanovna Vanina, ulitsa Tereshkovoi, 17, kv. 59, Moskovskaya oblast, Balashikha; Nadezhda Vasilievna Vdovenko, ulitsa Kapitanovskaya, 10, kv. 51, Kiev; Leonid Davidovich Melikadze, ulitsa Aratishvili, 8a, kv. 12, Tbilisi; Leonid Yakovlevich Malkes, ulitsa Danilevskogo, 16, kv. 30, Kharkov; Nikolai Grigorievich Vasiliev, ulitsa Kapitanovskaya, 6, kv. 8a, Kiev; Alexandr Sergeevich Borovikov, ulitsa Kravchenko, 4/1, kv. 21, Moscow, all of U.S.S.R.

[22] Filed: Feb. 13, 1974

[21] Appl. No.: 442,146

[52] U.S. Cl. .................................. 250/302; 73/104; 252/301.19; 252/408
[51] Int. Cl.² ................. G09K 11/06; G01N 19/08; G01N 21/16
[58] Field of Search ............... 252/408, 301.2 P; 73/104; 250/302

[56] References Cited

UNITED STATES PATENTS

| 2,806,959 | 9/1957 | De Forest et al. ....... 252/301.2 P X |
| 3,279,243 | 10/1966 | Molina ................. 73/104 |
| 3,560,399 | 2/1971 | Irsak .................. 252/301.2 P |
| 3,561,262 | 2/1971 | Borucki et al. ......... 252/301.2 P X |
| 3,751,970 | 8/1973 | Alburger ............... 252/301.2 P X |

FOREIGN PATENTS OR APPLICATIONS

| 362,860 | 12/1972 | U.S.S.R. |
| 137,294 | 1/1951 | U.S.S.R. |

Primary Examiner—Benjamin R. Padgett  
Assistant Examiner—David Leland  
Attorney, Agent, or Firm—Haseltine, Lake & Waters

[57] ABSTRACT

A method for detection of surface discontinuities by luminescence which consists in the successive treatment of the surfaces of materials subject to testing and inspection with the following compositions of a penetrant, cleaning fluid and a developer, whereupon they are inspected under an ultraviolet light at wavelength of 340–420 nm. Liquid constituents are in volume percent.

| a) penetrant | |
|---|---|
| ditolylmethane | 45–55 |
| lower aliphatic alcohol | 35–45 |
| surface-active substance of non-ionogenic type | 8–12 |
| 1,8-naphthoylene-1',2'-benzimidazole | 7–9 gr/l |
| or a composition: | |
| high-molecular aromatic hydrocarbons with boiling point of about 700° C | 15–20 |
| paraffin hydrocarbons with boiling point of 120–240° C | 80–85 |
| b) Cleaning Fluid | |
| lower aliphatic alcohol | 70–90 |
| surface-active substance of non-ionogenic type | 10–30 |
| c) developer | |
| acetone | 35–45 |
| white enamel based on collodion cotton | 25–35 |
| collodion | 25–35 |
| or a composition: | |
| bentonite clay in Na-form | 37–41 |
| lower aliphatic alcohol | 20–24 |
| water | 37–41 |
| kaolin | 56–60 gr/l |
| surface-active substance of non-ionogenic type | 3.4–3.7 gr/l |
| sodium nitrite | 2.4–2.8 gr/l |

The invention enables the revealing of surface discontinuities with a minimum width of 1–4 μm and provides adequate contrast and reliability in flow detection.

6 Claims, No Drawings

METHOD OF LUMINESCENCE DETECTION OF SURFACE DISCONTINUITIES

The present invention relates to a physical method of non-destructive control and, more particularly, to a method of detection of surface discontinuities by luminescence. The present method has proved to be advantageous in numerous branches of industry for inspecting critical parts made from different materials such as, metal, ceramic materials, glass, and the like in the course of production and operation.

Known in the art are various procedures for detecting surface discontinuities in the above-mentioned materials by luminescence wherein compounds forming a set are applied in succession to the surface of such materials which are then inspected under an ultraviolet light at wavelengths of 340–420 nm.

Usually the set includes:
a. Penetrant
b. Cleaning fluid
c. Developer.

Known in the art is a set for detecting luminescent flow comprising a penetrant which is a saturated solution of 1,8-naphthoylene-1′, 2′-benzimidazole in a mixture containing 50% of ditolylmethane, 40% of butyl alcohol and 10% of a surface-active substance; a cleaning compound which is a solvent, and a developer which is an aqueous suspension based on activated bentonite clay (see Inventor's Certificate of the USSR No. 196,423).

The above-described method of detecting surface discontinuities with the above-mentioned set is disadvantageous in that the set exhibits low sensitivity, inadequate reliability and poor contrast of the effects to be detected.

With the above-described method cracks from 5 to 6μm in width can be revealed and detected.

It is an object of the present invention to overcome the above disadvantages.

Accordingly, it is a primary object of the invention to provide new compositions comprising the penetrant, cleaning fluid and developer which ensure high quality and reliability in detecting surface discontinuities, such as cracks, oxide films, blowholes, etc.

The object is achieved by detecting surface discontinuities with luminescence by treating surfaces in succession with a penetrant, cleaning fluid and a developer and inspecting them under and ultraviolet light and wherein, according to the invention, the following composition is employed:

| a) Penetrant: | |
|---|---|
| ditolylmethane | 45–55 |
| lower aliphatic alcohol | 35–45 |
| surface-active substance of non-ionogenic type | |
| 1,8-naphthoylene-1′,2′-benzim/idazole | 8–12 |
| or a composition: | 7–9 g/l |
| high-molecular aromatic hydrocarbons with a b.p. of about 700° C | 15–20 |
| hydrocarbons of paraffin series with a b.p. of 120–240° C | 80–85 |
| b) Cleaning fluid | |
| lower aliphatic alcohol | 70–90 |
| surface-active substance of non-ionogenic type | 10–30 |
| c) Developer | |
| acetone | 35–45 |
| white enamel based on collodion cotton | 25–35 |
| collodion | 25–35 |
| or a composition: | |
| bentonite clay in Na-form | |
| lower aliphatic alcohol | 37–41 |
| water | 20–24 |
| kaolin | 37–41 |
| surface-active substance of non-ionogenic type | 56–50 g/l |
|  | 56–60 g/l |
|  | 3.4–3.7 g/l |
| sodium nitrite | 2.4–2.8 g/l |

Liquid components in compositions are given in volume percent

| Set No. 1 (liquid components are in vol. per cent) | |
|---|---|
| a) Penetrant | |
| ditolylmethane | 50 |
| lower aliphatic alcohol | 40 |
| surface-active substance of non-ionogenic type | 10 |
| 1,8-naphthoylene-1′,2′-benzimidazole | 8 g/l |
| b) Cleaning fluid | |
| lower aliphatic alcohol | 80 |
| surface-active substance of non-ionogenic type | 20 |
| c) Developer | |
| acetone | 40 |
| white enamel based on collodion cotton | 30 |
| collodion | 30 |
| Set No. 2 (liquid constituents are in volume per cent) | |
| a) Penetrant | |
| ditolylmethane | 50 |
| lower aliphatic alcohol | 40 |
| surface-active substance of non-ionogenic type | 10 |
| 1,8-naphthoylene-1′,2′-benzimidazole | 8 g/l |
| b) Cleaning fluid | |
| lower aliphatic alcohol | 80 |
| surface-active substance of non-ionogenic type | 20 |
| c) Developer | |
| bentonite clay in Na-form | 39 |
| lower aliphatic alcohol | 22 |
| water | 39 |
| kaolin | 58 |
| surface-active substance of non-ionogenic type | 3.5 g/l |
| sodium nitrite | 2.6 g/l |
| Set No. 3 (liquid constituents are in volume per cent) | |
| a) Penetrant | |
| high-molecular aromatic hydrocarbons with boiling point of about 700° C | 15 |
| paraffin hydrocarbons with boiling point of 120–240° C | 85 |
| b) Cleaning fluid | |
| lower aliphatic alcohol | 80 |
| surface-active substance of non-ionogenic type | 20 |
| c) Developer | |
| bentonite clay in Na-form | 39 |
| lower aliphatic alcohol | 22 |
| water | 39 |
| kaolin | 58 g/l |
| surface-active substance of non-ionogenic type | 3.5 g/l |
| sodium nitrite | 2.6 g/l |

All the specified components included in the sets are easily available, some of them being manufactured industrially in large quantities. The above-specified white enamel having a collodion cotton base is a mixture of collodion cotton and a white pigment, filler, plasticizer and a solvent also produced in heavy tonnage by the varnish and paint industry.

Collodion is a solution of nitrocellulose in a mixture of ethyl ether and ethyl alcohol, also produced by the chemical industry in large quantities.

The present invention offers the following advantages:

1. enhanced sensitivity — detection of surface discontinuities from 1 to 4μm wide and 30 μ and more deep depending on the set being used;
2. adequate contrast and reliability in detecting defects;
3. high inspection processability;
4. higher efficiency of inspection.

The herein-proposed method is accomplished in the following manner.

Parts to be tested are degreased in petrol, which is followed by subsequent washing in acetone and heating and cooling; or degreased in chlorinated hydrocarbons, such as trichloroethylene, without being heated and cooled. Then the penetrant is applied to the cooled surface by any known method, e.g., with a brush, and held for several minutes. The excess penetrant is removed with water and a cleaning fluid is applied also by any known method, e.g., with a brush, after which the parts are rinsed in warm water.

Moisture is removed from the surface to be tested by wiping it dry with an absorbent cloth, such as cotton print or coarse calico.

Following that, a developer is applied by any conventional method, e.g., by dipping, with a subsequent drying in a stream of heated air or in air at ambient temperature.

As soon as the developer dries, the parts are subjected to visual inspection under an ultraviolet light of a mercury-quartz lamp at wavelengths of 340–420 nm.

For a better understanding of the present invention given hereinbelow are illustrative examples of the embodiment of the present invention.

EXAMPLE 1

This example illustrates the use of the penetrant, cleaning fluid and developer of the following composition (liquid constituents are given in volume percent).

| | |
|---|---|
| a) Penetrant | |
| ditolylmethane | 50 |
| butyl alcohol | 40 |
| surface-active substance-monoethylamine treated with ethylene in the presence of a catalyst further referred to as OII-7 | 10 |
| 1,8-naphthoylene-1',2'benzimidazole | 8 g/l |
| b) Cleaning fluid | |
| ethyl alcohol | |
| surface active substance OII-7 | 20 |
| c) Developer | |
| acetone | 40 |
| white enamel based on collodion cotton | 30 |
| collodion | 30 |
| where: collodion is a solution of nitrocellulose in a mixture of ethyl ether and ethyl alcohol; white enamel based on collodion cotton has the following composition (non-volatile components are in weight parts): | |
| collodion cotton | 1 |
| camphor | 0.5 |
| castor oil | 0.86 |
| dibutyl phthalate | 0.44 |
| titanium dioxide | 0.9 |
| copper oleate | 0.01 |
| (volatile components are in weight per cent) | |

-continued

| | |
|---|---|
| butyl acetate or amyl acetate | 25 |
| acetone | 5 |
| butanol | 35 |
| toluene | 35 |

Parts from heat-resistant alloys with fine defects (cracks, oxide films, blowholes, pores, etc.) are subjected to degreasing first in petrol and then in acetone for 20–30 min. Then they are heated to a temperature of 80°–100° C (a temperature of 300°–350° C may be employed if the metal structure remains unchanged and no temper colors become manifest).

The degreased and cooled parts are immersed into the penetrant of the above-specified composition and held therein for 1–2 min. Following that, the parts are rinsed with warm water at a temperature of 30°–35° C and treated for 30–60 sec. with the cleaning fluid of the specified composition applied with a brush.

Total time of treatment with warm water and cleaning fluid ranges from 13 to 15 min.

After that, the parts are swept dry with absorbent cloth, such as cotton print or coarse calico, to provide complete removal of moisture. Then the developer is applied with a sprayer under a pressure of 2.5–4 atm to the dry prepared surface to produce a "wet" layer 10μm thick.

The part is inspected within 20–30 min after applying the developer under an ultraviolet light, the illumination ranging between 500–1,000 meter-candles.

To enable a comparative detection of surface discontinuities the above-specified parts were subjected to successive application of the penetrant, cleaning fluid and developer of the known composition and inspected under an ultraviolet light.

The defects revealed were evaluated according to a 5-point system. The work carried out in the above manner gave the following results.

1. Fine discontinuities, which in the above example amounted to 50%, were detected only with the aid of the specified set. The known set did not allow detecting said discontinuities.
2. The detection of larger surface discontinuities with the proposed set was evaluated at 5 points whereas that with the aid of the known set varied within 2–4 points.
3. The defects detected with the aid of the proposed set became manifest very clearly though a minimum width of the defects being revealed was about 1μ m and under. When using the known set, the outlines of the defects being detected were indistinct, which impeded appreciably proper classification of the defects.
4. The inspection of the parts with the aid of the proposed set ensures high reliability in detecting the defects which tend to recur during repeated inspection, the sensitivity and contrast remaining the same irrespective of the number of tests.

As to the reliability of inspection by the known method, it is low and the defects detected are revealed irregularly during repeated inspections.

EXAMPLE 2

The example given below illustrates the effectiveness of the following composition of the penetrant, cleaning fluid and developer (liquid constituents are in volume percent).

| a) Penetrant | |
| --- | --- |
| ditolymethane | 50 |
| butyl alcohol | 40 |
| surface-active substance OП-7 | 10 |
| 1,8-naphthoylene-1',2'-benzimidazole | 8 g/l |
| b) Cleaning fluid | |
| ethyl alcohol | 80 |
| surface-active substance OП-7 | 20 |
| c) Developer | |
| bentonite clay in Na-form (3.5% aqueous suspension) | 39 |
| ethyl alcohol | 22 |
| water | 39 |
| kaolin | 58 gr/l |
| surface-active substance OП-7 | 3.5 gr/l |
| sodium-nitrite | 2.6 gr/l |

All the technological operations, their sequence and holding time were similar to those utilized in Example 1 with the exception of the developer application operation. The developer was applied on a dry prepared surface in a thin layer with the aid of a sprayer under a pressure of from 2.5 to 4 atm.

The sensitivity, contrast and reliability of flow detection were also evaluated by comparing the above-specified characteristics with those obtained when treating the parts with the known compositions of the penetrant, cleaning fluid and developer, and further inspection under an ultraviolet light. The minimum width of the defects detected with the aid of the herein-proposed set is equal to 2–3μm, whereas with the use of the known compositions or sets the sensitivity was 5–6μm. With respect to the contrast and reliability of detection, they were similar to those attained in Example 1.

EXAMPLE 3

This example illustrates the following composition or set of penetrant, cleaning fluid and developer (liquid constituents are in volume percent).

| a) Penetrant | |
| --- | --- |
| high-molecular aromatic hydrocarbons with boiling point of about 700° C | 15 |
| kerosene | 85 |
| b) Cleaning fluid | |
| ethyl alcohol | 80 |
| surface-active substance OП-7 | 20 |
| c) Developer | |
| bentonite caly in Na-form (3.5% aqueous suspension) | 39 |
| ethyl alcohol | 22 |
| water | 39 |
| kaolin | 58 g/l |
| surface-active substance OП-7 | 3.5 g/l |
| sodium nitrite | 2.6 g/l |

All the technological operations, their sequence and holding time are similar to those used in Example 1 with the exception of the developer application operation which is similar to that employed in Example 2.

The sensitivity, contrast and reliability were evaluated also by comparing the above-specified characteristics with those obtained in testing the parts with the penetrant, cleaning fluid and developer of the known composition or set and subsequent inspection under an ultraviolet light.

The minimum width of the defects revealed with the aid of the herein-proposed set amounts to 3–4μm whereas the sensitivity attained with the known set ranges from 5 to 6μm. As for the contrast and reliability of detecting the defects, they are similar to those obtained in Example 1.

EXAMPLE 4

This example illustrates a composition or set of penetrant, cleaning fluid and developer similar to Example 1. The method was used for inspecting parts made from glass with fine defects (cracks, pores, etc.). The composition of the penetrant, cleaning fluid and developer, technological operations, their sequence and holding time were similar to those used in Example 1.

The sensitivity, contrast and reliability of detecting the defects were evaluated also by comparing the above-listed characteristics with those attained in applying the known compositions or sets of the penetrant, cleaning fluid and developer and subsequent inspection of the parts under an ultraviolet light. The minimum width of the defects revealed with the aid of the herein-proposed set amounts to 1–2μm, whereas with the use of the known compositions or sets it was equal to 5–6μm. The contrast and reliability attained in flow detection were similar to those obtained in Example 1.

What is claimed is:

1. A method of detecting surface discontinuities in materials, which are preferably metallic, with luminescence comprising treating the surface of said materials successively with a set of a penetrant, cleaning fluid and a developer and inspecting the treated surface under an ultraviolet light, said set having the following composition of penetrant, cleaning fluid and developer, the liquid constituents being in volume percent:

| a) Penetrant | |
| --- | --- |
| ditolylmethane | 45–55 |
| lower aliphatic alcohol | 35–45 |
| surface-active substance of non-ionogenic type | 8–12 |
| 1,8-naphthoylene-1',2'-benzimidazole | 7–9 g/l |
| b) Cleaning fluid | |
| lower aliphatic alcohol | 70–90 |
| surface-active substance of non-ionogenic type | 10–30 |
| c) Developer | |
| acetone | 35–45 |
| white enamel based on collodion cotton | 25–35 |
| collodion | 25–35 |

2. A method of detecting surface discontinuities in materials, which are preferably metallic, with luminescence comprising treating the surface of said materials successively with a set of a penetrant, cleaning fluid and a developer and inspecting the treated surface under an ultraviolet light, said set having the following composition of penetrant, cleaning fluid and developer, the liquid constituents being in volume percent:

| a) Penetrant | |
| --- | --- |
| high-molecular aromatic hydrocarbons with boiling points of about 700° C | 15–20 |
| paraffin hydrocarbons with boiling point of 120–240° C | 80–85 |
| b) Cleaning fluid | |
| lower aliphatic alcohol | 70–90 |
| surface-active substance of non-ionogenic type | 10–30 |
| c) Developer | |
| bentonite clay in Na-form | 37–41 |
| lower aliphatic alcohol | 20–24 |
| water | 37–41 |
| kaolin | 56–60 g/l |
| surface-active substance of non-ionogenic type | 3.4–3.7 g/l |

-continued

| | |
|---|---|
| sodium nitrite | 2.4–2.8 g/l. |

3. A method of detecting surface discontinuities in materials, which are preferably metallic, with luminescence comprising treating the surface of said materials successively with a set of a penetrant, cleaning fluid and a developer and inspecting the treated surface under an untraviolet light, said set having the following compositions of penetrant, cleaing fluid and developer, the liquid constituents being in volume percent:

| | |
|---|---|
| a) Penetrant | |
| ditolylmethane | 45–55 |
| lower aliphatic alcohol | 35–45 |
| surface-active substance of non-ionogenic type | 8–12 |
| 1,8-naphthoylene-1′, 2′-benzimidazole | 7–9 g/l |
| b) Cleaning fluid | |
| lower aliphatic alcohol | 70–90 |
| surface-active substance of non-ionogenic type | 10–30 |
| c) Developer | |
| bentonite clay in Na-form | 37–41 |
| lower aliphatic alcohol | 20–24 |
| water | 37–41 |
| kaolin | 56–60 g/l |
| surface-active substance of non-ionogenic type | 3.4–3.7 g/l |
| sodium nitrite | 2.4–2.8 g/l. |

4. A method according to claim 1, wherein the set of penetrant, cleaning fluid and developer have the following composition:

| | |
|---|---|
| a) Penetrant | |
| ditolylmethane | 50 |
| lower aliphatic alcohol | 40 |
| surface-active substance of non-ionogenic type | 10 |
| 1,8-naphthoylene-1′, 2′-benzimidazole | 8 g/l |
| b) Cleaning fluid | |
| lower aliphatic alcohol | 80 |
| surface-active substance of non-ionogenic type | 20 |
| c) Developer | |
| acetone | 40 |

-continued

| | |
|---|---|
| white enamel based on collodion | |
| cotton | 30 |
| collodion | 30. |

5. A method according to claim 2, wherein the set of penetrant, cleaning fluid and developer have the following composition:

| | |
|---|---|
| a) Penetrant | |
| high-molecular aromatic hydrocarbons with boiling point of about 700° C | 15 |
| paraffin hydrocarbons with boiling point of 120–24° C | 85 |
| b) Cleaning fluid | |
| lower aliphatic alcohol | 80 |
| surface-active substance of non-ionogenic type | 20 |
| c) Developer | |
| bentonite clay in Na-form | 39 |
| lower aliphatic alcohol | 22 |
| water | 39 |
| kaolin | 58 g/l |
| surface-active substance of non-ionogenic type | 3.5 g/l |
| sodium nitrite | 2.6 g/l. |

6. A method according to claim 3, wherein the set of penetrant, cleaning fluid and developer have the following composition:

| | |
|---|---|
| a) Penetrant | |
| ditolylmethane | 50 |
| lower aliphatic alcohol | 40 |
| surface-active substance of non-ionogenic type | 10 |
| 1,8-naphthoylene-1′, 2′-benzimidazole | 8 g/l |
| b) Cleaning fluid | |
| lower aliphatic alcohol | 80 |
| surface-active substance of non-ionogenic type | 20 |
| c) Developer | |
| bentonite clay in Na-form (3.5% aqueous suspension) | 39 |
| lower aliphatic alcohol | 22 |
| water | 39 |
| kaolin | 58 g/l |
| surface-active substance of non-ionogenic type | 3.5 g/l |
| sodium nitrite | 2.6 g/l. |

* * * * *